United States Patent [19]

Stevens

[11] Patent Number: 4,854,325

[45] Date of Patent: Aug. 8, 1989

[54] RECIPROCATING GUIDEWIRE METHOD

[76] Inventor: Robert C. Stevens, P.O. Box 250, Williston, Fla. 32696

[21] Appl. No.: 118,544

[22] Filed: Nov. 9, 1987

[51] Int. Cl.$^4$ .............................................. A61B 6/00
[52] U.S. Cl. .................................. 128/657; 128/772; 128/305; 604/164
[58] Field of Search ................... 128/303 R, 304, 305, 128/348.1, 656, 657, 772; 604/22, 54, 93, 95, 131, 156, 164

[56] References Cited

U.S. PATENT DOCUMENTS

| | | | |
|---|---|---|---|
| 3,352,303 | 11/1967 | Delaney | 128/303 R |
| 3,906,938 | 9/1975 | Fleischhacker | 128/772 |
| 4,223,676 | 9/1980 | Wuchinich et al. | 604/22 |
| 4,749,376 | 6/1988 | Kensey et al. | 128/305 |

Primary Examiner—Max Hindenburg
Assistant Examiner—Randy Citrin
Attorney, Agent, or Firm—Watts, Hoffmann Fisher & Heinke

[57] ABSTRACT

Guidewire insertion method and apparatus. A guidewire can be inserted into an obstructed blood vessel. A proximal portion of the guidewire is driven back and forth at high speed by a hand-held drive unit containing a battery, a D.C. motor and a transmission that converts rotating motor output shaft motion to reciprocating back and forth movement of a clamp that engages the guidewire. The guidewire moves back and forth at high speed within a catheter and a distal guidewire tip engages the obstruction with a ramming back and forth action to form a pilot passageway through the obstruction.

5 Claims, 5 Drawing Sheets

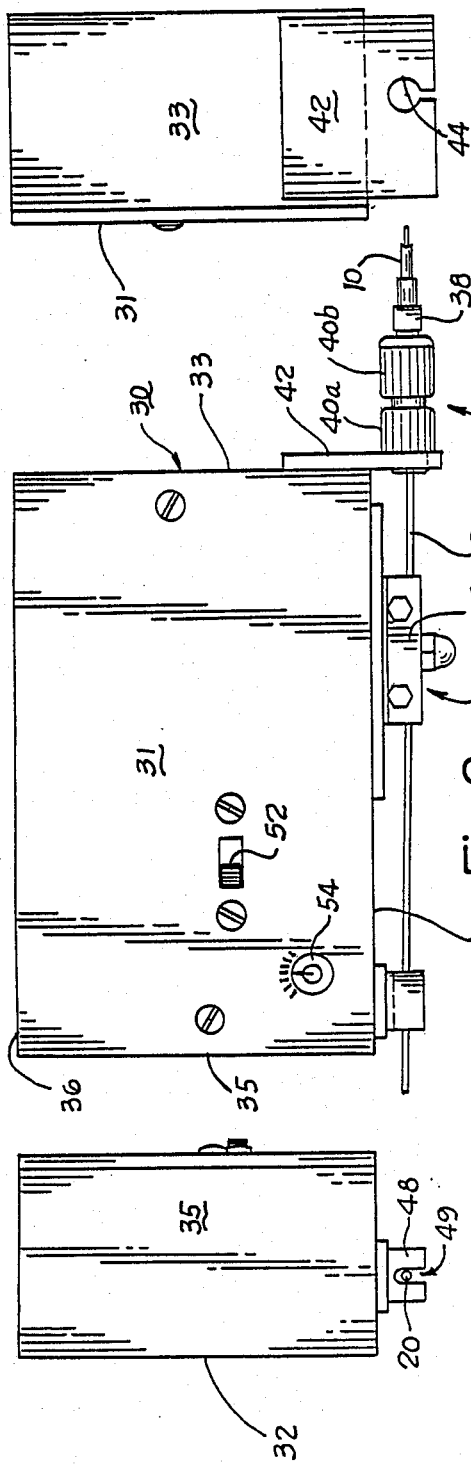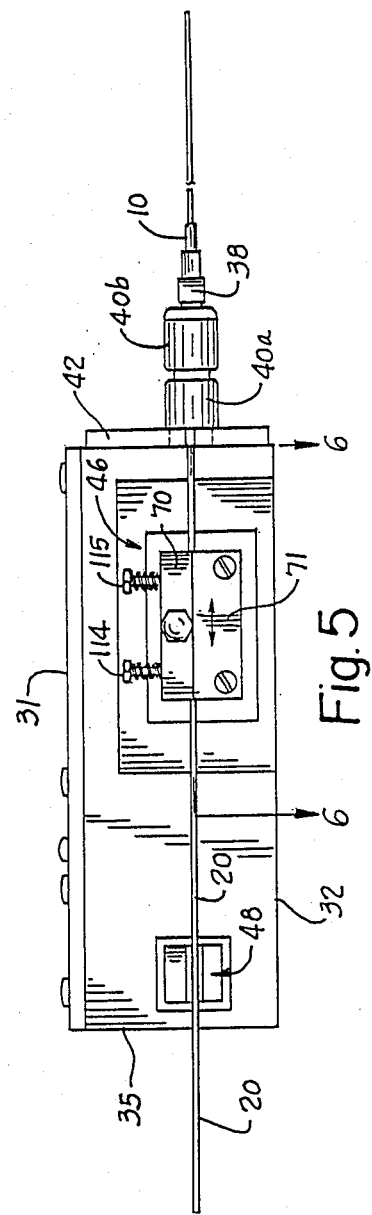

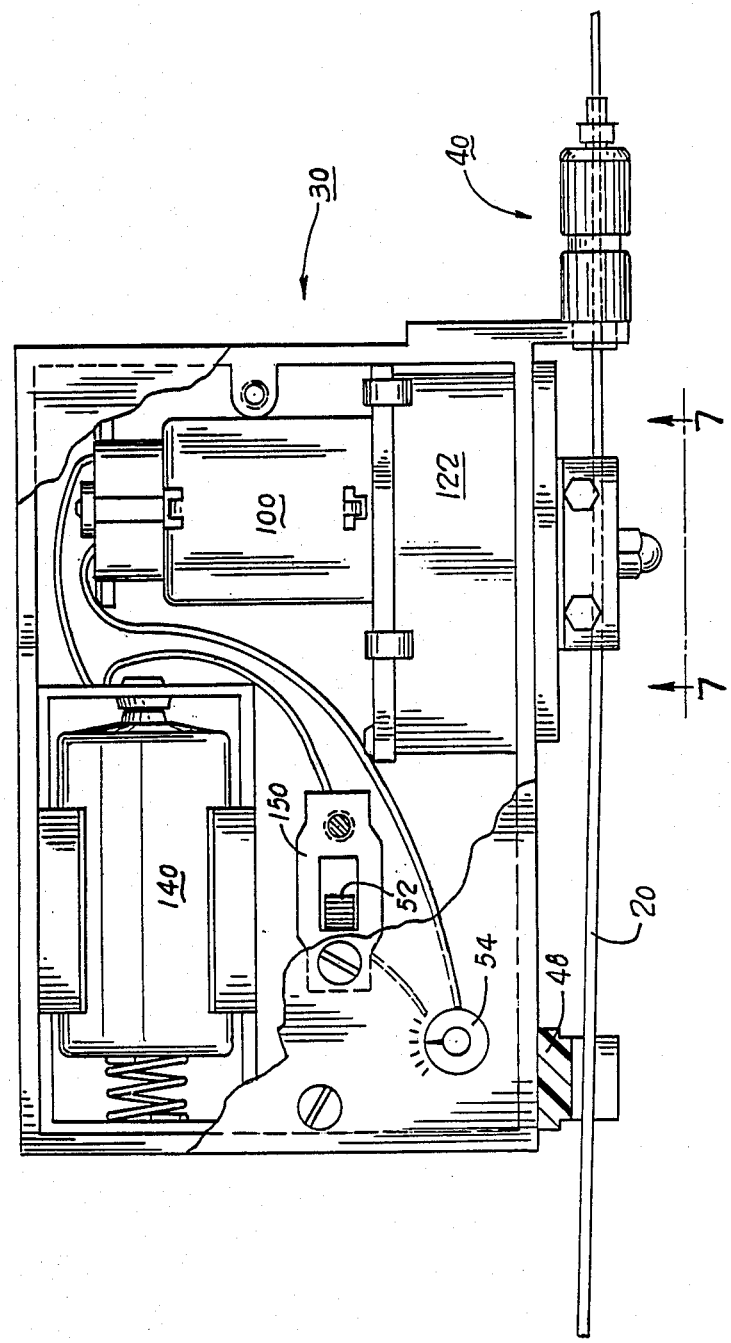

4,854,325

RECIPROCATING GUIDEWIRE METHOD

TECHNICAL FIELD

The present invention relates to a method and apparatus for inserting a flexible, elongated guidewire through a blocked patient blood vessel.

BACKGROUND ART

Elongated, flexible guidewires have been used in the prior art to position both diagnostic and therapeutic catheters within a patient. Catheters used in diagnostic angiography allow a contrast liquid to be injected through a catheter center passageway into a patient blood vessel to study blood flow patterns within the blood vessel. Coronary studies, for example, are typically conducted utilizing catheters which are positioned within the coronary artery with the aid of a flexible guidewire.

Within the last decade, specialized balloon catheters have been used to expand occluded blood vessels to increase blood flow through those vessels. The balloon catheter is inserted into the patient over the guidewire and properly positioned prior to its inflation.

The step of inserting a catheter, whether it is for diagnostic or therapeutic purposes, is often accomplished using a guidewire to steer the catheter into a proper position in the patient's cardiovascular system. The catheter's distal end can be more easily positioned if it follows the guidewire and is pushed over the guidewire to an appropriate position.

One prior art guidewire includes a distally located flexible tip portion that can be routed into the patient and maneuvered by monitoring progress of the guidewire on an x-ray imaging system. The distal tip can be constructed from a highly opaque material to facilitate this monitoring of the guidewire as it is inserted. Issued U.S. Pat. Nos. 4,545,390 to Leary and 4,538,622 to Samson et al. disclose representative prior art guidewire constructions.

Problems are often encountered as the physician attempts to route a guidewire through an obstructed region of a blood vessel while inserting a catheter. Prior art techniques for inserting the guidewire typically comprise the steps of jabbing the flexible distal tip portion of the guidewire against the obstructed region in hopes of finding a passageway through the obstruction. If the blood vessel is totally blocked by plaque or the like, these efforts fail and it becomes impossible to route the catheter to a proper position.

DISCLOSURE OF THE INVENTION

The present invention relates to both method and apparatus for aiding a physician in routing a guidewire through an obstruction. In accordance with the disclosed technique, when the attending physician experiences difficulty in routing the guidewire through a blood vessel obstruction, a hand-held vibrating drive is attached to the proximal portion of the guidewire outside the patient and energized to impart rapid back and forth transverse movement to a distal guidewire tip. As the guidewire rapidly translates back and forth the physician again brings the guidewire tip into contact with the obstruction which bores a pilot hole through the obstruction.

Apparatus for rapidly reciprocating the guidewire includes a clamp that frictionally engages an outer surface of the guidewire outside the patient. A hand-held drive mechanism is coupled to the clamp and reciprocates the clamp back and forth at high speed causing the guidewire to reciprocate back and forth through a guide catheter that isolates all but a distal portion of the guidewire from the inner wall of the blood vessel. When the guidewire tip encounters the obstruction the high speed reciprocating motion of the tip causes the guidewire to force its way through the obstruction. Once the guidewire has been pushed through an obstruction the physician disconnects the clamp and continues to manually insert the guidewire. If other obstructions are encountered the clamp is again attached to the guidewire and used to force the distal guidewire tip through those other obstructions.

A preferred embodiment of the invention includes a hand-held motor powered by a battery and contained in a small compact housing. A transmission is coupled to an output shaft of the motor to convert rotation of a motor output shaft into a reciprocating back and forth movement of the guidewire. An adjustment allows the physician to control the rate of reciprocating movement in a range of from 1000 to 5000 cycles per minute (approximately 15-85 cycles per second).

A preferred clamp defines first and second relatively movable members having confronting surfaces biased towards each other by a spring. These surfaces define an elongated groove or gap to accommodate the guidewire. In operation, the physician manually retracts one of the movable members, inserts the guidewire into the gap and allows the spring to bias the two confronting surfaces toward each other to trap the guidewire in place. The unit is then energized to cause the clamp to reciprocate back and forth at the desired speed as the physician continues to insert the guidewire.

From the above it is appreciated that one object of the invention is a mechanism to facilitate insertion of a guidewire through blood vessel obstructions and more particularly relates to a mechanism for imparting rapid back and forth translational movement to the guidewire as the guidewire is routed to a desired location within the patient. This and other objects, advantages and features of the invention will become better understood from a detailed description of the invention which is described in conjunction with the accompanying drawings.

BRIEF DESCRIPTION OF THE DRAWINGS

FIG. 2 is a plan view of a hand-held device for applying reciprocating back and forth movement to a proximally located portion of the guidewire;

FIGS. 3 and 4 are end elevation views of the FIG. 2 device;

FIG. 5 is a side elevation view of the hand-held device;

FIG. 9 is a partially sectioned plan view of the hand-held device.

BEST MODE FOR CARRYING OUT THE INVENTION

Figure 1:
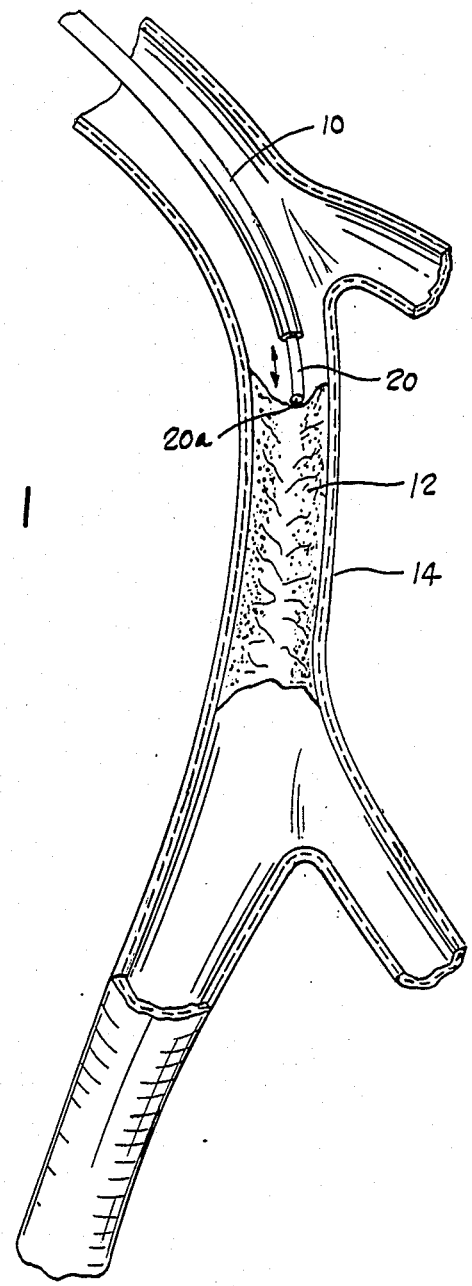
FIG. 1 is a schematic of a guide catheter and guidewire approaching an obstructed region of a patient blood vessel.

Turning now to the drawings, FIG. 1 schematically illustrates an elongated catheter 10 approaching an obstruction 12 in a blood vessel 14. The catheter 10 is inserted with the aid of a guidewire 20 passing through a center passageway extending from the proximal to the distal end of the catheter 10. Techniques for inserting and routing flexible elongated guidewires through a patient's cardiovascular system are known in the prior art.

Figure 1A:
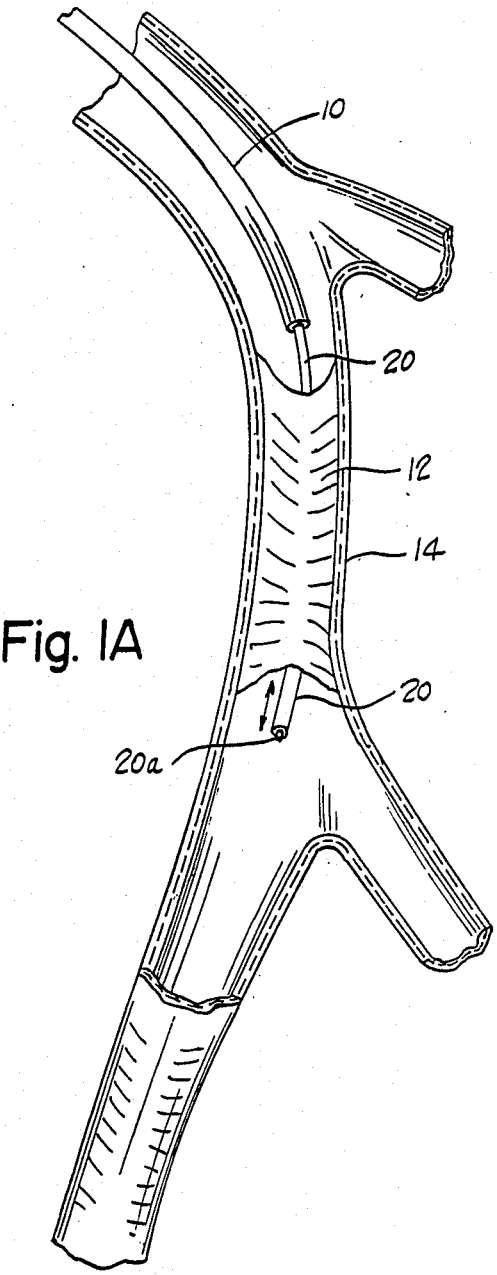
FIG. 1A is a schematic showing the distal portion of the guidewire extending through the obstructed region of the patient blood vessel.

In accordance with the present invention, if an obstructed region is encountered during insertion of the guidewire 20, a guidewire tip portion 20a is driven at high speed with a back and forth movement to cause the distal tip portion 20a of the guidewire to contact the obstruction with a back and forth ramming motion. This causes the guidewire to enter and pass through the obstruction 14 (FIG. 1A) forming a pilot passageway through the obstruction. Once the pilot passageway is formed, the catheter 10 can also be pushed through the obstruction.

The catheter 10 can be a balloon catheter, an angiographic catheter or a special thin walled guide catheter used to allow the guidewire to be reciprocated at high speed without contacting the inner walls of the patient cardiovascular system. The forming of a passageway through the obstruction with the reciprocating guidewire may be used to increase circulation in peripherals that otherwise would require amputation due to poor circulation. Forming a pilot hole may be sufficient to increase circulation or this technique may be used in conjunction with a catheter having a high speed rotating or reciprocating working head that may be pushed through the obstruction 12 once the pilot passageway is formed with the guidewire 20.

FIGS. 2–5 illustrate a portable drive unit 30 coupled to a proximal end of the catheter 10 for reciprocating the guidewire 20 back and forth through the catheter 10. The drive unit 30 defines a box-like housing having top and bottom walls 31, 32 and four side walls 33–36. (FIG. 2). A leur fitting 38 coupled to the proximal end of the catheter 10 is attached to the drive unit 30 by a coupling 40 including a male 40a and a female 40b leur attachment. The guidewire 20 extends through a center passageway in both attachments 40a, 40b. A bracket 42 that extends from a front wall 33 of the drive unit 30 has a slotted opening 44 for mounting the male attachment 40a to the drive unit 30.

Typical prior art guidewires are up to 2 meters long. Since the physician has not completed the task of inserting the catheter and guidewire a substantial portion of the guidewire remains exposed, outside the patient. A clamp 46 extending from the wall 34 engages an exposed outer surface of the guidewire 20 and reciprocates the guidewire back and forth through the catheter 10. To help position the guidewire 20 during this back and forth reciprocating motion, the drive unit 30 includes a guide 48 which defines a channel 49 to help position the guidewire 20. This prevents the guidewire from flopping back and forth in an uncontrolled fashion during high speed back and forth translation of the guidewire by the clamp 46.

The drive unit 30 has dimensions that are small enough to allow the attending physician to easily maneuver the box-like housing seen in FIG. 2. Extending through a top wall 31 are an on/off switch actuator 52 and continuously variable speed control 54. The fact that the drive unit 30 is easily maneuverable by the attending physician allows it to be re-oriented with respect to the patient and to accommodate different patient entry points for the catheter 10 and guidewire 20.

With the catheter 10 secured to the drive unit 30 via the coupling 40, the distal tip (FIG. 1) of the catheter 10 can be moved in and out along the tortuous passageway leading to the obstruction by manipulation of the drive unit 30. By pushing the drive unit toward an entryway where the guidewire and catheter enter the patient, the distal portion of the catheter 10 can be pushed into the patient. Similarly, by pulling the drive unit away from the entry point, the distal tip can be backed away from the obstructed region.

As seen most clearly in FIGS. 5–8, the guidewire clamp 46 comprises top and bottom plastic clamp members 70, 71 and a clamp guide 72 (FIG. 6) that is mounted to a shaft 80 which extends through the drive unit wall 34. The shaft 80 oscillates back and forth and comprises a portion of a transmission 90 coupled to a motor 100.

The top clamp member 70 is coupled to the clamp guide 72 by a threaded connector 102 which extends through the clamp member 70 and fixes the clamp member 70 to the translating clamp guide 72. The bottom clamp member 71 is movably connected to the top clamp member 70 by two connectors 104, 105 that extend through vertical passageways 110, 111 in the top clamp member 70. The connectors 104, 105 are fixed with respect to the clamp member 71 since they are screwed into threaded openings in the clamp member 71, but slide up and down in relation to the clamp member 70. The bottom clamp member 71 is biased toward the clamp member 70 by two compression springs 112, 113 trapped between enlarged heads 114, 115 of the two connectors 104, 105 and a top surface 117 of the top clamp member 70.

Figure 6:
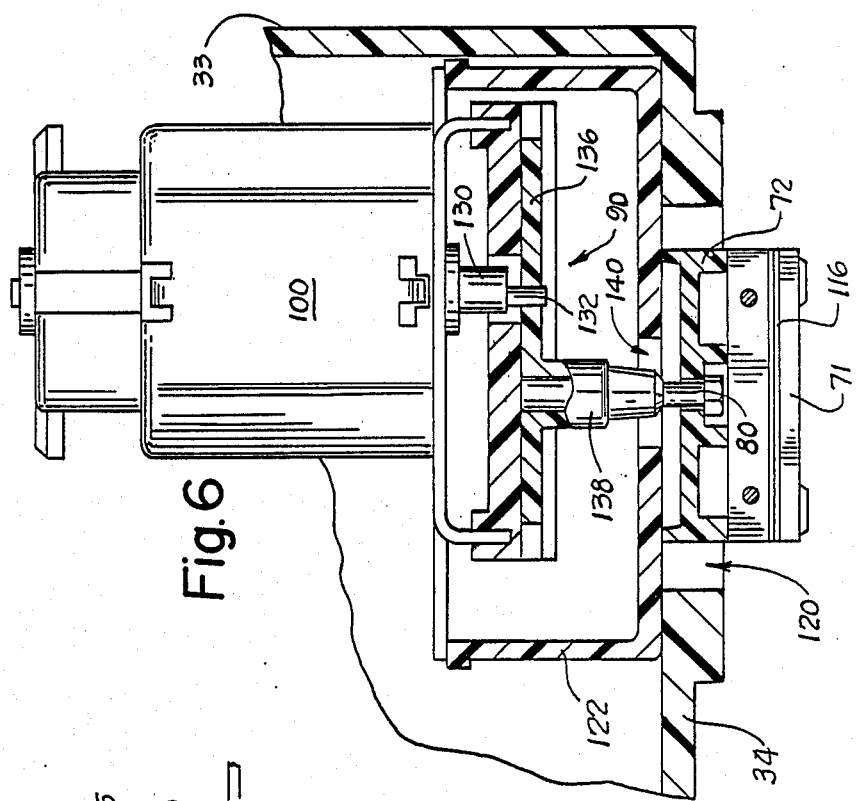
FIG. 6 is a partially sectioned view taken along the line 6—6 in FIG. 5.
Figure 7:
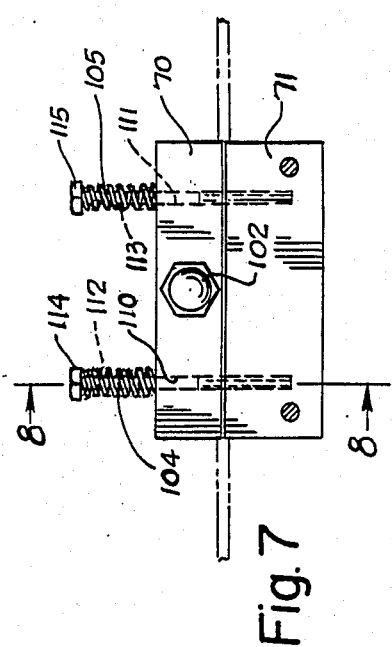
FIG. 7 is an enlarged plan view of a clamp for engaging the guidewire.
Figure 8:
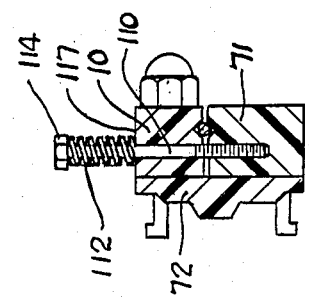
FIG. 8 is a section view as seen from the plane defined by the line 8—8 in FIG. 7.

Inner surfaces of the two clamp members 70, 71 define a groove that frictionally engages the guidewire to enable the drive unit 30 to effect a back and forth translational movement of the guidewire with respect to the catheter 10. A notched groove 116 in the bottom clamp member 71 is seen in FIG. 6. The groove 116 extends the entire width of the clamp member 71 so that the clamp member 71 can be displaced a distance from the clamp member 70 and the guidewire slipped through an entryway temporarily formed between the two clamp members 70, 71 and fit within the generally square shaped opening defined by the two aligned notches. Once the clamp member 71 is released the springs 112, 113 clamp the guidewire within the members 70, 71 and the guidewire is secured for back and forth movement with the clamp 46.

As seen in FIG. 6, the wall 34 defines an opening 120 to accommodate back and forth movement of the clamp guide 72. The transmission 90 is housed within a housing 122 fixed with respect to the motor 100. The transmission 90 includes an eccentric drive 130 for converting rotational output from a motor shaft (not shown) into a back and forth translational movement of the clamp 46. An eccentric shaft 132 rotates about an axis coincident with the center axis of the motor output shaft. Due to the off-center position of the shaft 132 a back and forth as well as an up and down movement is imparted to a plate 136 mounted to the shaft 132. Integrally molded with the plate 136 is a cylindrical support 138 which passes through an opening 140 in the transmission housing 122. The shaft 80 that drives the clamp guide 72 back and forth is connected to the support 138, passes through an opening in the clamp guide 72 and is fixed to the clamp guide 72. Back and forth movement applied to the shaft 132 from the eccentric 130 is transmitted to the plate 136, cylindrical support 138 and shaft 80.

Turning now to FIG. 9, the drive motor 100 is electrically coupled to a battery 140 for applying an energization voltage to the motor 100. A preferred motor comprises a direct current variable speed motor capable of producing rotational speeds at an output shaft coupled to the eccentric 130 of the range 1,000 to 5,000 rpm. The switch actuator 52 is coupled to a switch body 150 having switch contacts that are opened and closed in response to operation of the actuator 52. With the contacts closed a battery voltage is applied across the series combination of the motor 100 and a variable resistance potentiometer adjusted by the speed control 54. By actuating the switch actuator 52 and adjusting the setting of the speed control 54 it is possible for the physician to adjust the speed of back and forth movement of the clamp 46 and guidewire 20.

The diameter of the eccentric drive 130 dictates the amount of back and forth guidewire movement per cycle. A preferred range of total back and forth movement is 1/16 to ⅛ inch. This amount of movement can be reduced to approximately 1/32 of an inch for small diameter blood vessels such as for coronary studies and increased for larger diameter blood vessels up to a range of approximately ¼ inch for peripherals.

Once the guidewire 20 is fixed in the clamp 46 with the catheter 10 attached to the catheter coupling 40, the relative position of the guidewire distal tip 20a with respect to a distal end of the catheter sheath is fixed until the motor 100 is energized to translate the guidewire back and forth. If the physician determines the relative position of the distal tip 20a and catheter is inappropriate, the guidewire 20 can be pushed or pulled through the catheter since the engagement between the guidewire outer surface and the clamp members 70, 71 is a frictional engagement and can easily be overcome by the attending physician.

The catheter 10 can be a balloon catheter, an angiographic catheter, or a specially designed thin-walled catheter used only during guidewire insertion. The catheter isolates back and forth movement of the guidewire from the blood vessel lining along a major portion of the guidewire length. Only the distal tip portion of the guidewire is exposed within the blood vessel. It is anticipated, for example, that the distal tip of the guidewire will extend beyond the catheter 10 from between 1 to 15 cm. during high speed back and forth translational movement of the guidewire.

In operation, the attending physician positions the guidewire 20 and catheter 10 using convention prior art procedures with the aid of an x-ray viewing system. If difficulties in positioning the guidewire 20 are encountered, the coupling 40 is placed over the proximal part of the guidewire 20 and attached to the catheter's leur fitting 38. The guidewire is then slipped through a slot 44a into the opening 44 and the male attachment 40a secured to the bracket 42. The guidewire 20 is then positioned relative the catheter 10 until a desired length of guidewire extends beyond the distal end of the catheter 10. The guidewire 20 is then fixed to the clamp 46 and the motor 100 energized. Finally, the repetition rate of oscillations can be adjusted via the speed control 54. The rapidly reciprocating distal tip 20a forces its way through the obstruction as the physician pushes the guidewire forward.

Although a preferred embodiment of the invention has been described utilizing a thin-walled catheter, it is appreciated that the techniques disclosed have applicability for use with a balloon catheter, for example. It is the intent therefore that the invention include all modifications and variations from the disclosed embodiment falling within the spirit or scope of the appended claims.

I claim:

1. A method for positioning a guidewire in a subject passageway comprising the steps of:
   (a) inserting an elongated guidewire into a subject and monitoring passage of a distal tip of said guidewire through a subject passageway on a viewing screen; and
   (b) in the event difficulty is encountered while positioning said guidewire, attaching a reciprocating drive to a portion of the guidewire located outside the subject and actuating the drive to reciprocate the guidewire back and forth a distance of from 1/32 to ¼ inch at a frequency of from 1000 to 5000 cycles per minute to move the distal end of the guidewire back and forth into contact with an obstruction causing the difficulty while continuing to position the guidewire in the obstruction.

2. The method of claim 1 where the back and forth movement of the guidewire is shielded from the passageway along a length of the guidewire extending from an entry point of said guidewire into the subject to all but a short distal portion of said guidewire.

3. A method for forcing a guidewire through a subject blood vessel obstruction comprising the steps of:
   (a) inserting an elongated guidewire into a patient's cardiovascular system and monitoring passage of a distal tip of said guidewire through the blood vessel on a viewing screen; and
   (b) in the event difficulty is encountered while inserting said guidewire, attaching a reciprocating drive to a portion of the guidewire located outside the subject and actuating the drive to reciprocate the guidewire back and forth a distance of from 1/32 to ¼ inch at a frequency of from 1000 to 5000 cycles per minute to move the distal end of the guidewire into back and forth contact with an obstruction causing the difficulty so that the guidewire forms a pilot passageway in the obstruction.

4. The method of claim 3 where the back and forth movement of the guidewire is shielded from the blood vessel along a length of the guidewire extending from an entry point of said guidewire into the subject to all but a short distal portion of said guidewire.

5. The method of claim 4 wherein the shielding step is accomplished with an elongated catheter which is also pushed through the obstruction subsequent to the forming of the pilot passageway.

* * * * *